United States Patent [19]

Bogaty et al.

[11] Patent Number: 4,559,057
[45] Date of Patent: Dec. 17, 1985

[54] PROCESS AND COMPOSITION FOR COLORING HAIR WITH PIGMENTS

[75] Inventors: Herman Bogaty, Chapel Hill, N.C.; Keith Brown, New Canaan; Norman P. Loveless, Bethel; Leszek J. Wolfram, Stamford, all of Conn.

[73] Assignee: Clairol Incorporated, New York, N.Y.

[21] Appl. No.: 509,909

[22] Filed: Jul. 1, 1983

[51] Int. Cl.[4] .................................................. A61K 7/13
[52] U.S. Cl. ............................................ 8/405; 8/554; 8/637; 8/606; 424/DIG. 1; 424/DIG. 2
[58] Field of Search .......................... 8/405, 554, 637; 424/DIG. 2

[56] References Cited

U.S. PATENT DOCUMENTS

| | | | |
|---|---|---|---|
| 3,592,581 | 7/1971 | Shawsky et al. | 8/405 |
| 3,711,316 | 1/1973 | Angliss et al. | 8/128 A |
| 3,743,622 | 7/1973 | Wagner et al. | 8/405 |
| 3,790,512 | 2/1974 | Wagner et al. | 8/405 |
| 3,912,808 | 10/1975 | Sokol | 8/127.51 |
| 3,973,901 | 8/1976 | Micchelli et al. | 8/425 |
| 3,986,825 | 10/1976 | Sokol | 8/406 |
| 4,027,008 | 5/1977 | Sokol | 8/111 |
| 4,047,888 | 9/1977 | Papantoniou | 8/411 |
| 4,091,113 | 5/1978 | Green et al. | 564/295 |
| 4,150,115 | 4/1979 | Jacquet et al. | 424/70 |
| 4,182,612 | 1/1980 | Sokol et al. | 8/426 |
| 4,357,141 | 11/1982 | Grollier et al. | 8/406 |
| 4,422,853 | 12/1983 | Jacquet et al. | 8/406 |

FOREIGN PATENT DOCUMENTS 721045 12/1954 United Kingdom .

*Primary Examiner*—A. Lionel Clingman
*Attorney, Agent, or Firm*—Gabriel P. Katona

[57] ABSTRACT

A process and composition for coloring human hair on the head with pigments that employ a dispersion of pigment or pigments in an aqueous alcoholic liquid medium that contains a cationic polymer that is compatible with the aqueous alcoholic medium.

29 Claims, No Drawings

PROCESS AND COMPOSITION FOR COLORING HAIR WITH PIGMENTS

This invention relates to a process for hair coloring and to compositions useful for this purpose. More particularly, it concerns processes and compositions that employ pigments as the colorants.

It is often desirable to be able to color hair on the human head quickly. One way of accomplishing this is to apply pigments to the hair under conditions which will deposit the pigment on the hair fiber. Pigments, by definition, are insoluble in the liquid media normally used in application of coloring materials to the hair. They therefore do not penetrate into the hair fiber as is the case with conventional hair dyes and remain distributed on the fiber surfaces.

When pigments are deposited onto a hair surface from ordinary liquid media, the adherence of the colorant to the surface is poor. The pigment color is, as a consequence, readily transferred to clothing, skin, combs, brushes, and other surfaces with which it comes in contact. This tendency to "rub-off" or "crock" has been a major disadvantage in the use of pigments for hair coloring.

It has now been found that the rub-off of pigment colored hair can be significantly reduced if the pigment is applied to the hair from an aqueous alcoholic medium containing an appropriate cationic polymer compatible with the aqueous alcoholic medium. While cationic polymers are generally useful in decreasing the "rub-off" of the pigment color, certain types containing amino or quaternary ammonium groups are particularly effective in this regard especially when used at optimum concentration.

Apart from providing rub-off protection for the pigment colored hair, it is important that the physical characteristics of the hair after coloring treatment be esthetically acceptable. Thus, for example, the feel of the hair and its luster must meet consumer acceptability standards. The process of the present invention leaves the hair with an acceptable feel and luster and with enhanced setting properties useful in maintaining the hair style configuration.

It is accordingly an object of the present invention to provide a process for coloring hair employing pigments in which the pigment applied shows a minimum of rub-off and leaves the hair with acceptable feel and luster.

It is still a further object of the present invention to provide a composition which may be used to reach the aforesaid objects.

Other and more detailed objects of this invention will be apparent from the following description and claims.

While Shansky et al (U.S. Pat. No. 3,592,581) have employed water-insoluble phthalocyanine dyestuffs in aqueous media containing small amounts of benzyl alcohol and quaternary ammonium surfactants for hair coloring, their compositions are quite different from the present invention. The benzyl alcohol used by Shansky et al is present in low concentrations (1-4%) and used in the capacity of a solvent for the dye. Moreover, the cationic component used is a monomeric surfactant. In contrast, our compositions employ much higher concentrations of alcohols in which the pigments are not soluble and the cationic components of our compositions are polymeric. These differences significantly alter the character and mode of pigment deposition leading (in our case) to materially superior dye-outs and hair esthetics.

The U.S. Pat. No. 3,711,316 to Angliss et al relates to a process for coloring textile material consisting partly or wholly of wool or other keratinous fibers that makes use of pigment dyes. In accordance with this patent, it provides a process for the pigment dyeing of "wool or other materials consisting wholly or partly of keratin fibers" which involves treating the material with a polymer or mixture of polymers containing pigments in finely dispersed form so as to coat the fibers. The pigment dispersion is then dried on the fibers which is then followed by a treatment with another polymer to form an overcoating which is then cured. The polymer may be applied from an aqueous solution or emulsion which may contain a wetting agent. By way of illustrating suitable polymers that may be employed, the patentees only suggest "a mixture of a polyamide epichlorohydrin resin and etherified methylol melamine resin". In applying their polymer system to their fabric, the patentees use a temperature which minimally is at least as hot as steam (100° C.) and upwards to 150° C. The patentees also highly recommend chlorinating the fabric before pigment dyeing.

The Angliss et al process is significantly different from the present process in many respects. In the first place, it is concerned with dyeing fabrics and not hair on the human head. Secondly, the pigment is not applied from an aqueous alcoholic medium as is the case with the present invention. Thirdly, the temperature that it employs is much higher than can be tolerated by the human head. Fourthly, the patented process calls for the application of an overcoat which, if applied to hair, would give the hair an unacceptable texture, aside from adding to the complexity of the process by additional steps in processing.

As pointed out above, a feature of the present invention resides in the use of an aqueous alcoholic medium from which the pigment is to be applied to the human head. The terms "alcohol" or "alcoholic" are used in their usual generic sense to refer to the class of alcohols. Any of a number of alcohols may be used in formulating the aqueous alcoholic medium that may be employed in the present invention. By way of example, there may be mentioned ethyl alcohol, isopropyl alcohol, benzyl alcohol, methyl cellosolve, butyl cellosolve, etc. Because of its cosmetic acceptability and the fact that it decreases interfacial tension between pigment particle and the polymer solution, ethanol is a preferred alcohol for use in this invention. This improved wetting facilitates the formation of the pigment dispersion and its stability.

The ratio of alcohol to water in the aqueous alcoholic medium may vary. This will, to a large extent, be determined by the level of pigment in the system. Generally, the alcohol to water ratio by volume of the aqueous alcoholic medium will be in the range of from about 1:10 to about 50:1. More usually, this range will be from about 1:1 to about 3:1 with the preferred range being from about 1.2:1 to about 2:1.

Another feature of the present invention is the incorporation of a cationic polymer in the aqueous alcoholic liquid medium. An important characteristic of the cationic polymer selected is its compatability with the aqueous alcoholic medium at the concentration at which the polymer is employed. As used herein, the term "compatability" refers to the ability of the cationic polymer to resist separation from the aqueous alcoholic medium.

The cationic polymers compatible with the aqueous alcohol medium are generally useful in increasing the resistance to rub-off of the dyed hair. Particularly effective are cationic polymers containing amino or quaternary ammonium groups and a variety of such polymers are known. These include dibasic acid diethylenetriamine type copolymers which may be described by the general formula:

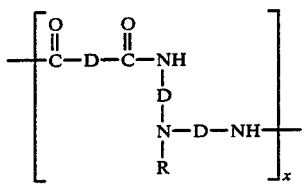

(I)

wherein D is divalent alkylene radical e.g. —CH$_2$—CH$_2$— (preferably a lower divalent alkylene radical having from 1 to 6 carbon atoms), R is an alkyl or substituted alkyl radical having preferably up to 10 carbon atoms; and x is the degree of polymerization. These are exemplified by adipic acid/dimethylaminohydroxypropyl diethylenetriamine copolymer (Cartaretin F-4; Sandoz) and adipic acid/epoxypropyl diethylenetriamine copolymer (Delsette 101; Hercules). General formulas for these materials are given in the Cosmetic & Ingredient Dictionary, Third edition, 1982, p. 7 published by the Cosmetic, Toiletry and Fragrance Association Inc., Washington, D.C.

Another variety of cationic polymer that is useful for the purposes of the present invention is the polymeric quaternary ammonium salts that conform to the formula:

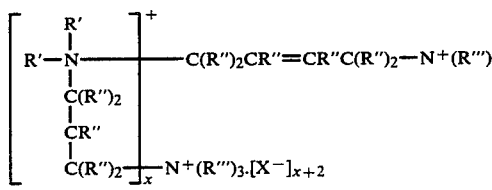

(II)

wherein:
R' is lower alkyl, and preferably methyl;
R" is hydrogen or lower alkyl, and preferably hydrogen;
R''' is lower hydroxyalkyl, and preferably hydroxyethyl;
X is halogen, and preferably Cl; and
x is the degree of polymerization.

In the case where R' or R" are lower alkyl in Formula II, they may contain up to 6 and preferably up to 4 carbon atoms. Similarly, the lower hydroxyalkyl radical R''' of Formula II may contain up to 6 carbon atoms with the number preferably being up to 4 carbon atoms.

An example of a polymeric quaternary ammonium salt conforming to Formula II above that is available commercially is sold under the trade designation "Onamer M". The CTFA designation for this material given in the Cosmetic Ingredient Dictionary, Third Edition, 1982 published by the Cosmetic, Toiletry and Fragrance Association Inc. Washington, D.C. is POLYQUATERNIUM-1. The formula for POLYQUATERNIUM-1 is given as:

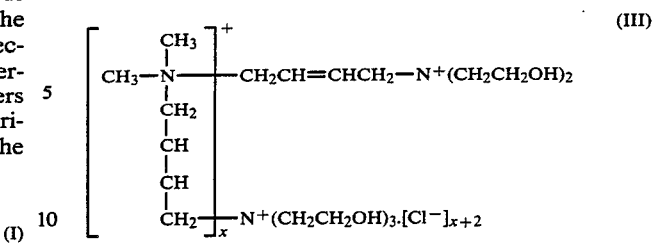

(III)

Still another variety of cationic polymer that may be used in the present invention are the quaternized polymers of a vinylic pyridine (QPVP). Of this class of cationic polymers, the preferred material is the polymer prepared from 4-vinyl pyridine which is quaternized with CH$_3$Cl or CH$_3$I. These ordinarily will have a molecular weight in excess of about 50,000 and are between 60% to 100% quaternized.

In the case of the quaternized polyvinyl pyridines, the compatability of the cationic polymer with the aqueous alcohol medium may vary with the quantity of this material employed. Thus, the amount of alcohol tolerated by QPVP is best determined by experiment since it depends on degree of quaternizing of the particular QPVP.

The quantity of cationic polymer that will be contained in the composition employed in this invention may vary somewhat. Usually, however, this will be present at a level of the order of about from 0.1% to about 20% solids by weight based on the total weight of the composition. In the preferred practice, the cationic polymer will comprise from about 2.5% to about 5.0% solids by weight based on the total weight of the dyeing composition.

The process of the present invention can make use of wide selection of pigments. These can be inorganic or organic pigments but the best results have been obtained with organic pigments. Typical inorganic pigments that may be employed for the present purposes include iron and other metal oxides, and carbon black.

As for the organic pigments, these may be used singly or in combination. It will often be necessary to use a blend of pigments to obtain natural looking shades. Typical classes of organic pigments that are utilizable for the present purposes include the phthalocyanines, quinacridones, azo pigments and xanthenes. Some of the commercially available pigments that may be used are listed below:

| Designation | Chemical Class |
|---|---|
| RT-139 (DuPont) (CI 15865:2) | Azo |
| D&C Red 9 (Kohnstamm) (CI 15585:1) | Azo |
| Saugatuck Red (BASF) (CI 15602) | Azo |
| Sandorin Red (Sandoz) (Pigment Red) | Xanthene |
| D&C Red 36 (Kohnstamm) (CI 12085) | Azo |
| Red RT-769P (DuPont) (CI 46500) | Quinacridone |

Some pigment dyestuffs are commercially available in the moist state known as "Presscake". This form is useful in formulating compositions in that the particle size is small and dispersion in the compositions occurs readily.

The quantity of pigment that will be incorporated in the compositions utilized in the present invention may, of course, vary with the color results that are desired. Usually, however, this will constitute between from about 0.01% to about 10% solids by weight based on the total weight of the dyeing composition with the preferred range being from about 0.03% to about 7.0% solids by weight on the same weight basis.

In preparing the pigments for incorporation in the compositions of the present invention, it is well to reduce the particle size of the pigment, by grinding or other technique, to a size that gives a relatively stable dispersion when the pigment is distributed in the liquid medium. A particle size range for pigment which has been found to be useful is from about $0.01\mu$ to about $10\mu$ with the best results being obtained when the range is from about $0.01\mu$ to about $1.0\mu$.

In some instances, some benefit in ease of application may be obtained by the incorporation of a thickener in the dyeing composition. Non-soluble thickeners have been found to be the most useful. These are exemplified by such materials as Veegum and Syloid.

The mechanism by which the incorporation of a cationic polymer in an aqueous alcoholic pigment dispersion reduces the degree of rub-off and increases the luster of the hair is not fully understood. It is thought, however, that the presence of the cationic polymer causes the pigment particles laid down on the hair to be effectively encapsulated and thus, the tendency of individual particles to agglomerate into larger clusters is decreased. As a consequence, the tendency for the pigment particles to be rubbed off is reduced. This encapsulation also has the effect of increasing the luster of the pigment.

In preparing the compositions of the present invention, a solution of the cationic polymer in water is mixed with alcohol (absolute) with agitation. This forms a suspension or solution of the cationic polymer in the aqueous-alcoholic medium depending on the concentration of alcohol used. The pigments usually in the form of a presscake are then dispersed in the cationic polymer composition. Several of the well known dispersion methods may be used to accomplish this using equipment such as Waring micro-blender, ball mill or high speed disperser.

In applying the pigment composition to the human head, a quantity of pigment dispersion sufficient to thoroughly wet the hair is applied to the head. This is generally done at ambient temperatures. The dye composition is maintained in contact with the hair for various time periods depending on the color results desired. Usually, this will be for about from 1 min. to about 20 min. with the preferred treatment time being from about 1 min. to about 10 min. The hair is then rinsed thoroughly with water and dried. Hot air drying is the preferable mode for drying.

The following Examples are given to further illustrate the present invention. It is to be understood, however, that the invention is not limited thereto.

EXAMPLE 1

Preparation of Delsette/Ethanol Vehicle 73.68 g of absolute ethanol (SDA-40) were added to 26.32 g Delsette 101 (12.5% solids in water) with agitation. The milky white suspension that results is stable on standing.

Preparation of Pigment Dispersions

Pigment or pigment mixtures were dispersed into the Delsette/ethanol/water system in one of the following ways:

(a) Waring Micro-blender 1.48 g Waxoline Black OBP Pigment (ICI) was added to 98.52 g of the above Delsette/ethanol/water suspension and blended for 5–10 minutes at medium speed. The black suspension was stored in a closed container until needed.

(b) Ball Mill 4.42 g Dalamar Y-839-P (29.4% solids, DuPont) and 7.08 g Monastral RT-763P (38.5% solids, DuPont) pigments are placed in a wide mouthed plastic jar with a solution of 9.75 g Cartaretin F 4 (30% solids in water) in 78.75 g ethanol. Stainless steel balls (⅛" diameter) are added and the mixture shaken in a commercial paint shaker for 30 minutes. The orange/red dispersion was decanted from the balls and stored.

(c) High Speed Dispersion

A mixture of the following pigments:

0.10 g Monastral BT-482P (CI 74160) (58.6% solids, DuPont)

0.28 g Monastral RT-763P (CI 46500) (38.9% solids)

0.11 g Dalamar YT-763P (CI 11741) (29.4% solids)

0.22 g Chromophthal Brown 5R (Pigment Brown 23) (100% Ciba-Geigy)

0.87 g Brown V presscake (CI 15800:2) (26% solids, Hilton Davis)

was placed in a beaker with 98.42 g of the Delsette 101/ethanol/water suspension and dispersed with a Tekmar SD 45 disperser for 15 minutes. During this time the beaker was externally cooled (ice) and covered to prevent solvent evaporation. The brown stable suspension was stored in a closed container until required.

These dispersing techniques could be used interchangeably since they produced no significant variation in particle size or dispersion stability.

EXAMPLE 2

A 2 g swatch of blended gray hair was immersed in 2 g of the dispersion of Example 1(a) for 5 minutes. The swatch was then rinsed under running water and dried with a hair dryer. It was dyed a medium gray color which was resistant to water bleeding but totally removed by shampoo.

EXAMPLE 3

The dyeout procedure of Example 2 was repeated with the pigment dispersion of Example 1(b) to give a medium auburn shade which could be removed by shampooing.

EXAMPLE 4

The dyeout procedure of Example 2 was repeated with pigment dispersion of Example 1(c). Gray hair was dyed ash brown.

EXAMPLE 5

The following materials were mixed and dispersed by the method of Example 1(a) and dyed out by the method of Example 2:

| | |
|---|---|
| Monastral BT-482-P | 0.20% |
| Dalamar YT-889-P | 0.20% |
| Sandorin Red BN (100% solids, Sandoz) | 0.30% |
| Delsette 101 | 26.21% |
| Ethanol | 73.08% |
| Fragrance | 0.01% |
| | 100.00% |

The gray hair was dyed medium brown.

EXAMPLE 6

The following materials were dispersed by the method of Example 1(c) and dyed out by the method of Example 2:

| | |
|---|---|
| Monastral BT-482-P | 0.11% |
| Dalamar YT-889-P | 1.32% |
| Monastral RT-139 (60% solids) | 0.86% |
| Delsette 101 | 25.76% |
| Ethanol | 71.94% |
| Fragrance | 0.01% |
| | 100.00% |

Gray permanently waved hair was dyed medium auburn by this composition.

EXAMPLE 7

The following materials were dispersed by the method of Example 1(a) and dyed out by the method of Example 2:

| | |
|---|---|
| Monastral BT-482-P | 2.0% |
| Monastral RT-763-P | 2.0% |
| Onamer M (30% solids, Onyx) | 11.0% |
| Ethanol | 56.0% |
| Water | 29.0% |
| | 100.0% |

White hair was dyed royal blue by this composition.

EXAMPLE 8

The following materials were dispersed by the method of Example 1(a):

| | |
|---|---|
| Dalamar YT-839-P | 0.98% |
| Monastral RT-763-P | 6.99% |
| Monastral BT-482-P | 1.14% |
| Veegum (Vanderbilt) | 3.00% |
| Delsette 101 | 22.45% |
| Ethanol | 65.43% |
| Fragrance | 0.01% |
| | 100.00% |

This suspension was much thicker than those prepared in the previous Examples and was applied to a gray swatch by the "combing through" technique. After rinsing and drying, the swatch was dyed to a light gray shade.

EXAMPLE 9

The following materials were dispersed by the method of Example 1(a):

| | |
|---|---|
| Monastral BT-482-P | 0.29% |
| Monastral RT-763-P | 0.80% |
| Dalamar YT-839-P | 0.14% |
| Delsette 101 | 8.64% |
| Water | 65.80% |
| Isopropanol | 24.17% |
| | 100.00% |

White hair was dyed a medium brown shade by this composition.

EXAMPLE 10

The following materials were dispersed by the method of Example 1(a):

| | |
|---|---|
| Cosmetic Yellow (Sun Chemical) (CI 77492) | 4.65% |
| Monastral BT-482-P | 0.47% |
| Cartaretin F-4 | 11.00% |
| Water | 41.94% |
| Ethanol | 41.94% |
| | 100.00% |

Gray hair was dyed medium gray by this composition.

"Cationic polymers" as described above are employed in this invention to enhance the adhesion of the desired pigment color to the hair fiber as well as to provide other described cosmetic and esthetic benefits to the dyed hair. While cationic polymers as a broad class are effective for these purposes, those containing amine and quaternary ammonium groupings are particularly effective in minimizing the rub-off of pigment from the colored hair. A simple rub-off test was devised which appeared to correlate well with on-the-head dyeing results and is described below.

Rub-Off Test

A dry pigmented hair tress, approximately 4-5 inches long, is laid on a flat surface. A 2 cm area from a roll of white adhesive tape (Johnson & Johnson Co.) is rubbed over the length of the dyed tress ten times with a uniform firm pressure. The amount of color which is transferred from the hair to the tape is visually evaluated. The degree of rub-off is classified as high, moderate, or low. Low rub-off is designated when little or no color can be seen on the tape. High rub-off signifies that the color on the tape is as intense (or more intense) than the color on the dyed hair tress. Dyeings which show low or moderate rub-off are considered as showing satisfactory rub-off resistance characteristics for the purposes of this invention, and have been found to be satisfactory under practical use conditions. Rub-off from the hair swatch of Example 6 was very low as measured by this test. However, when the Delsette 101 in this composition was replaced by an equivalent amount of cationic surfactant (Aromox DMC or Arquad S-50; Armak Industries) not only was the color intensity on the hair lower but the rub-off was high.

Although the invention has been described with reference to specific forms thereof, it will be understood that many changes and modifications may be made without departing form the spirit of this invention.

What is claimed is:

1. A process for coloring hair on the human head with a liquid composition containing one or more pigments which comprises:
   (a) forming a dispersion consisting essentially of an effective coloring amount of said pigment in an aqueous alcoholic liquid medium containing a cationic polymer having amino or quaternary groups; said cationic polymer being compatible with said aqueous alcoholic medium and said pigment being insoluble in said alcohol; the ratio by volume of alcohol to water in said aqueous alcoholic medium being in the range of from about 1:10 to about 50:1;
   (b) applying said dispersion to said hair at a temperature that is tolerated by the live human scalp and for a time sufficient to deposit an effective coloring amount of said pigment on said hair.

2. A process according to claim 1 in which said composition is applied to said hair by combing it through the hair.

3. A process according to claim 1 in which the hair is dried after application of said dispersion.

4. A process according to claim 1 in which said composition is applied to the hair for a period of from about 1 to 20 minutes.

5. A process according to claim 4 wherein said time of application is in the range of from about 1 minute to about 10 minutes.

6. A process according to claim 1 in which said hair is rinsed after the application of said composition and then subjected to a drying step.

7. A process according to claim 1 in which the ratio by volume of alcohol to water in said aqueous alcoholic medium is in the range of from about 1:1 to about 3:1.

8. A process according to claim 7 in which the ratio by volume of alcohol to water in said aqueous alcoholic medium is in the range of from about 1.2:1 to about 2:1.

9. A process according to claim 1 in which the cationic polymer is of the following structure:

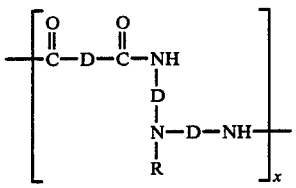

wherein:
(a) D is a divalent $C_{1-6}$ alkylene radical;
(b) R is $C_{1-10}$ alkyl or substituted $C_{1-10}$ alkyl; and
(c) x is the degree of polymerization where X is 2 or more.

10. A process according to claim 1 in which said cationic polymer is of the formula:

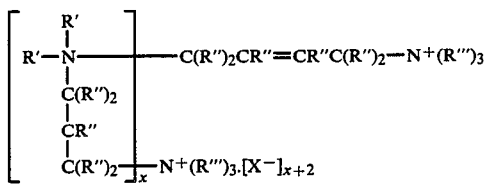

wherein:
(a) R' is $C_{1-6}$ alkyl;
(b) R'' is hydrogen or $C_{1-6}$ alkyl;
(c) R''' is $C_{1-6}$ hydroxyalkyl;
(d) X is halogen; and
(e) x is the degree of polymerization where X is 2 or more.

11. A process according to claim 1 in which said cationic polymer is a quaternized polyvinylic pyridine.

12. A composition for coloring hair on the human head which comprises:
(a) a dispersion consisting essentially of an effective coloring amount of a pigment in an aqueous alcoholic liquid medium containing a cationic polymer having amino or quaternary ammonium groups; said cationic polymer being compatible with said aqueous alcoholic medium and said pigment being insoluble in said alcohol;
(b) the ratio by volume of alcohol to water in said aqueous alcoholic medium being in the range of from about 1:10 to about 50:1.

13. A composition according to claim 12 in which the ratio by volume of alcohol to water in said aqueous alcoholic medium is in the range of from about 1:1 to about 3:1.

14. A composition according to claim 13 in which the ratio by volume of alcohol to water in said aqueous alcoholic medium is in the range of from about 1.2:1 to about 2:1.

15. A composition according to claim 12 in which said cationic polymer is of the formula:

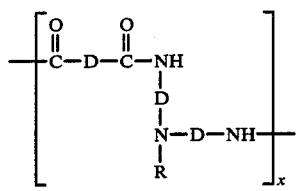

wherein:
(a) D is a divalent $C_{1-6}$ alkylene radical;
(b) R is $C_{1-10}$ alkyl or substituted $C_{1-10}$ alkyl; and
(c) x is the degree of polymerization where X is 2 or more.

16. A composition according to claim 12 in which said cationic polymer is of the formula:

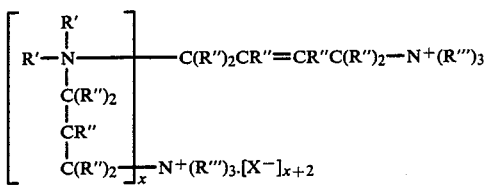

wherein:
(a) R' is $C_{1-6}$ alkyl;
(b) R'' is hydrogen or $C_{1-6}$ alkyl;
(c) R''' is $C_{1-6}$ hydroxyalkyl;
(d) X is halogen; and
(e) x is the degree of polymerization where X is 2 or more.

17. A composition according to claim 12 in which said cationic polymer is a quaternized polyvinylic pyridine.

18. A composition according to claim 12 in which said pigment is present in said composition at a level in the range of from about 0.01% to about 10% solids by weight based on the total weight of said composition.

19. A composition according to claim 18 in which said cationic polymer is present in said composition at a level in the range of from about 0.1% to about 20% solids by weight based on the total weight of said composition.

20. A composition according to claim 12 in which said pigment is present in said composition at a level within the range of from about 0.03% to about 7% solids by weight based on the total weight of said composition.

21. A composition according to claim 20 in which said cationic polymer is present in said composition at a level in the range of from about 2.5% to about 5% solids by weight based on the total weight of said composition.

22. A process according to claim 1 wherein said cationic polymer is selected from the group consisting of adipic acid/dimethylaminohydroxypropyl diethylenetriamine copolymer; adipic acid epoxypropyl diethylenetriamine copolymer, Polyquaternium-1, and quaternized polymer of 4-vinyl pyridine.

23. A process according to claim 22 wherein said pigment is selected from the group consisting of metal oxides, carbon black, phthalocyanine pigments, quinacridone pigments, azo pigments and xanthene pigments.

24. A composition according to claim 12 wherein said cationic polymer is selected from the group consisting of adipic acid/dimethylaminohydroxypropyl diethylenetriamine copolymer, adipic acid/epoxypropyl diethylenetrianime copolymer, Polyquaternium-1, and quaternized polymer of 4-vinyl pyridine.

25. A composition according to claim 24 wherein said pigment is selected from the group consisting of metal oxides, carbon black, phthalocyanine pigments, quinacridone pigments, azo pigments and xanthene pigments.

26. A process according to claim 1 in which the liquid composition also contains a thickener.

27. A process according to claims 1 or 26 in which the liquid composition also contains a fragrance.

28. A composition according to claim 12 wherein said dispersion also contains a thickener.

29. A composition according to claims 12 or 28 in which said dispersion also contains a fragrance.

* * * * *